(12) United States Patent (10) Patent No.: US 12,656,325 B2

Wang (45) Date of Patent: Jun. 16, 2026

(54) WATER QUALITY DETECTION SYSTEM

(71) Applicant: Huawei Technologies Co., Ltd., Shenzhen (CN)

(72) Inventor: Zhenwei Wang, Shenzhen (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 53 days.

(21) Appl. No.: 18/512,692

(22) Filed: Nov. 17, 2023

(65) Prior Publication Data

US 2024/0085395 A1 Mar. 14, 2024

Related U.S. Application Data

(63) Continuation of application No. PCT/CN2022/084915, filed on Apr. 1, 2022.

(30) Foreign Application Priority Data

May 18, 2021 (CN) .......................... 202110540810.6

(51) Int. Cl.
*G01N 33/18* (2006.01)
*G01J 3/02* (2006.01)
(Continued)

(52) U.S. Cl.
CPC .......... *G01N 33/1826* (2013.01); *G01J 3/021* (2013.01); *G01J 3/0218* (2013.01);
(Continued)

(58) Field of Classification Search
CPC ....... G01N 33/1826; G01N 2021/6417; G01N 2201/062; G01N 21/94; G01N 33/1893;
(Continued)

(56) References Cited

U.S. PATENT DOCUMENTS 5,048,960 A * 9/1991 Hayashi .................... G01J 3/42
356/319
5,192,980 A * 3/1993 Dixon ................ G02B 21/0076
356/334
(Continued)

FOREIGN PATENT DOCUMENTS

CN 101013136 A 8/2007
CN 103245644 A 8/2013
(Continued)

OTHER PUBLICATIONS

Sima, Weichang: "Study on the Method of Detecting Fluorescent Signal and the Circuit Design for Chlorophyll Fluorometer Using Multi-wavelength LED Array", Thesis, Jun. 1, 2007, XP009541806, pp. 1-68.

*Primary Examiner* — Abdullahi Nur

(74) *Attorney, Agent, or Firm* — Slater Matsil, LLP

(57) ABSTRACT

A water quality detection system including a light source, a spectrometer, and a data processor is disclosed, and relates to the technical field of detection systems. The light source emits excitation light pulse trains of different wavelengths to a to-be-detected water sample contained in a sample cell, where the excitation light pulse trains of different wavelengths may be emitted in a time-division manner, to excite the to-be-detected water sample, thereby generating fluorescence separately corresponding to the excitation light pulse trains of different wavelengths. The spectrometer receives the fluorescence and output a fluorescence spectrum based on the fluorescence. The data processor obtains, based on the fluorescence spectrum output by the spectrometer, a three-dimensional fluorescence spectrum including an excitation wavelength, a fluorescence wavelength, and a fluorescence intensity, identifies the to-be-detected water sample and (Continued)

obtains a parameter of the to-be-detected water sample based on the three-dimensional fluorescence spectrum.

20 Claims, 9 Drawing Sheets

(51) Int. Cl.

| | | |
|---|---|---|
| *G01J 3/10* | (2006.01) | |
| *G01J 3/44* | (2006.01) | |
| *G01N 21/64* | (2006.01) | |

(52) U.S. Cl.
CPC .............. *G01J 3/0243* (2013.01); *G01J 3/10* (2013.01); *G01J 3/4406* (2013.01); *G01N 21/6402* (2013.01); *G01N 21/6408* (2013.01); *G01N 21/645* (2013.01); *G01N 2021/6417* (2013.01); *G01N 2021/6419* (2013.01); *G01N 2021/6421* (2013.01); *G01N 2021/6463* (2013.01); *G01N 2021/6484* (2013.01); *G01N 2201/062* (2013.01)

(58) Field of Classification Search
CPC ........... G01N 2201/0627; G01N 21/01; G01N 2021/0112; G01J 3/02; G01J 3/28; G01J 3/26
See application file for complete search history.

(56) References Cited

U.S. PATENT DOCUMENTS

| | | | |
|---|---|---|---|
| 7,139,071 B2 | 11/2006 | Bennett et al. | |
| 7,858,911 B2 * | 12/2010 | Fairley .................. | G02B 27/40 |
| | | | 250/201.3 |
| 8,319,978 B2 * | 11/2012 | Ben-Levi ............. | G02B 21/008 |
| | | | 356/601 |
| 8,922,762 B2 * | 12/2014 | Yamazaki .......... | G02B 27/1066 |
| | | | 356/73 |
| 9,671,345 B2 | 6/2017 | Manian | |
| 10,317,281 B2 | 6/2019 | Wang et al. | |
| 2005/0084980 A1 * | 4/2005 | Koo ........................... | G01J 3/44 |
| | | | 436/171 |
| 2007/0070333 A1 * | 3/2007 | Klinkhammer ...... | G01N 21/645 |
| | | | 356/213 |
| 2008/0304048 A1 * | 12/2008 | Tormod ................. | G01N 21/33 |
| | | | 356/442 |
| 2009/0213362 A1 * | 8/2009 | Nakamura ................. | G01J 3/36 |
| | | | 356/72 |
| 2009/0268203 A1 * | 10/2009 | Uzunbajakava .......... | G01J 3/02 |
| | | | 356/436 |
| 2012/0228518 A1 * | 9/2012 | Rigneault .......... | G01N 21/6456 |
| | | | 250/206 |
| 2015/0029326 A1 * | 1/2015 | Backman .............. | G01J 3/1256 |
| | | | 348/80 |
| 2019/0018115 A1 | 1/2019 | Schmitt et al. | |
| 2019/0025215 A1 | 1/2019 | Ameloot et al. | |
| 2020/0209208 A1 * | 7/2020 | Li ....................... | H01L 25/0753 |

FOREIGN PATENT DOCUMENTS

| | | | |
|---|---|---|---|
| CN | 103616354 A | 3/2014 | |
| CN | 103868901 A | 6/2014 | |
| CN | 105548128 A | 5/2016 | |
| CN | 205844192 U | 12/2016 | |
| CN | 104198391 B | 2/2017 | |
| CN | 106872424 A | 6/2017 | |
| CN | 107631983 A | 1/2018 | |
| CN | 107831155 A | 3/2018 | |
| CN | 109085149 A | 12/2018 | |
| CN | 109655110 A | 4/2019 | |
| CN | 112557358 A | 3/2021 | |
| WO | 2000016149 A1 | 3/2000 | |

* cited by examiner

Excitation wavelength/nm

Fluorescence wavelength/ nm

WATER QUALITY DETECTION SYSTEM

CROSS-REFERENCE TO RELATED APPLICATIONS

This application is a continuation of International Application No. PCT/CN2022/084915, filed on Apr. 1, 2022, which claims priority to Chinese Patent Application No. 202110540810.6, filed on May 18, 2021. The disclosures of the aforementioned applications are hereby incorporated by reference in their entireties.

TECHNICAL FIELD

This application relates to the field of spectrum detection technologies, and in particular, to a water quality detection system.

BACKGROUND

With rapid development of industrial production in human society, water environment pollution is becoming increasingly severe and poses a threat to human health and ecological security. Therefore, abatement of water environment pollution has become a key research topic for sustainable industrial development in the future.

For abatement of water environment pollution, first, it is required to establish an online monitoring system for key observation sites (including a key pollution source and a basin observation site) to monitor a pollution situation continuously and automatically. At present, this online monitoring system mainly monitors comprehensive indexes of water quality. Key pollution indexes are mainly measured by using a chemical method or a spectrum detection method. However, measurement through the chemical method produces a lot of chemical waste liquids, which easily causes secondary pollution. However, during use of the spectrum detection method, an established prediction model needs to be recalibrated based on different water quality, resulting in poor universality.

Based on this, currently, how to provide a universal water quality measurement method for real-time online detection while reducing water environment pollution is a technical problem to be urgently resolved by a person skilled in the art.

SUMMARY

This application provides a water quality detection system. The water quality detection system is universal, and can perform real-time online detection on water quality, thereby improving detection accuracy.

According to a first aspect, this application provides a water quality detection system. The water quality detection system includes a light source, a spectrometer, and a data processor. The light source may emit excitation light pulse trains of different wavelengths to a to-be-detected water sample in a sample cell in a time-division manner. In this way, the excitation light pulse trains of different wavelengths may separately excite the to-be-detected water sample, to generate fluorescence separately corresponding to the excitation light pulse trains of different wavelengths. The spectrometer may be configured to: receive the fluorescence, and output a fluorescence spectrum based on the fluorescence. The data processor may be configured to: obtain, based on the fluorescence spectrum output by the spectrometer, a three-dimensional fluorescence spectrum including an excitation wavelength, a fluorescence wavelength, and a fluorescence intensity, determine and identify, based on the three-dimensional fluorescence spectrum, whether a pollution component or component proportion of the to-be-detected water sample changes, and obtain a parameter of the to-be-detected water sample based on the three-dimensional fluorescence spectrum.

According to the water quality detection system provided in this application, a change of a water quality model (a pollution component in a water sample) can be monitored while a key pollutant parameter of water quality is measured, and a warning function is provided, to remind operation and maintenance personnel to calibrate a device in a timely manner, thereby avoiding a detection failure of the water quality detection system when the water quality model changes. Therefore, universality of the water quality detection system is improved.

In a possible implementation of this application, total duration of emitting an excitation light pulse train of each wavelength may be 100 ms to 10 s, for example, 500 ms. Such pulse driving can reduce power consumption of the light source and facilitate heat dissipation of the light source.

In a possible implementation of this application, in the excitation light pulse trains of different wavelengths emitted by the light source to the to-be-detected water sample in a time-division manner, a time interval $\Delta t$ between a cutoff time of emitting an excitation light pulse train of a previous wavelength and a start time of emitting an excitation light pulse train of a current wavelength may be 100 ms to 1 s, for example, 500 ms. The time interval $\Delta t$ may be specifically set based on an application scenario of the water quality detection system.

In addition, a wavelength difference between excitation light pulse trains of two different wavelengths emitted by the light source to the to-be-detected water sample at the time interval $\Delta t$ is 5 nm to 30 nm. On the basis of reducing mutual influence between the excitation light pulse trains of different wavelengths, fluorescence generated by exciting the to-be-detected water sample by an excitation light pulse train of each wavelength can be obtained.

In a possible implementation of this application, the water quality detection system further includes a reflection element, and the reflection element may be disposed between the light source and the sample cell. The excitation light pulse trains of different wavelengths emitted by the light source may be emitted into the to-be-detected water sample through the reflection element. In addition, the fluorescence obtained through excitation by the excitation light pulse trains of different wavelengths may enter the spectrometer through the reflection element. Through disposing of the reflection element, transmission paths of the excitation light pulse trains of different wavelengths and a transmission path of the fluorescence can be adjusted, thereby improving efficiency of collecting the fluorescence by the spectrometer.

In addition, the water quality detection system may further include a first lens assembly. The first lens assembly may be disposed between the reflection element and the sample cell, and the first lens assembly may be configured to focus the excitation light pulse trains of different wavelengths on the to-be-detected water sample. The first lens assembly may include an achromatic lens, so that focal points of the excitation light pulse trains of different wavelengths focused by the first lens assembly are basically the same in the sample cell, thereby improving detection precision of the water quality detection system.

The water quality detection system may further include a second lens assembly, and the second lens assembly is disposed between the reflection element and the spectrometer and is configured to focus the fluorescence reflected by the reflection element and then input the focused fluorescence into the spectrometer, so that the fluorescence can be received by the spectrometer as much as possible.

In a possible implementation of this application, a pinhole filter may be further disposed between the second lens assembly and the spectrometer. The pinhole filter has a pinhole, and the pinhole and a focal point of the excitation light pulse train in the to-be-detected water sample are conjugated. In this way, the pinhole may filter out fluorescence and a background stray light signal that are generated outside the focal point at a bottom of the sample cell. In this way, the fluorescence reflected by the reflection element is only fluorescence excited at the focal point in the to-be-detected water sample, and the fluorescence is focused on the pinhole by the second lens assembly and is input into the spectrometer after passing through the pinhole.

A third lens assembly may be further disposed between the pinhole filter and the spectrometer. The third lens assembly may be configured to collimate and focus the fluorescence that passes through the pinhole filter and then input the collimated and focused fluorescence into the spectrometer, so that the fluorescence is received by the spectrometer as much as possible, thereby improving detection accuracy.

In a possible implementation of this application, the spectrometer of the water quality detection system may be a fiber optic spectrometer. In this case, the pinhole filter and the third lens assembly may not be disposed. In this implementation, the fluorescence reflected by the reflection element may be focused by the second lens assembly and then directly enter the fiber optic spectrometer through a fiber optic of the fiber optic spectrometer, thereby simplifying a structure of the water quality detection system.

In this application, the reflection element is disposed in a plurality of manners. For example, the reflection element is a beam splitter, and the beam splitter may be configured to transmit a part of the excitation light pulse trains of different wavelengths emitted by the light source. In addition, the beam splitter may be configured to change a transmission direction of the fluorescence, so that the fluorescence can enter the spectrometer.

In a possible implementation of this application, a focal point of the excitation light pulse trains of different wavelengths focused by the first lens assembly is located at the bottom of the sample cell, where the sample cell is used to carry the to-be-detected water sample. The excitation light pulse trains of different wavelengths may be reflected by the bottom of the sample cell and then received by the spectrometer after passing through the to-be-detected water sample. In addition, the data processor may be further configured to obtain an absorption spectrum based on the excitation light pulse trains of different wavelengths received by the spectrometer, to obtain the parameter of the to-be-detected water sample based on the absorption spectrum. In this implementation, an optical path of the reflected excitation light pulse train and an optical path of the fluorescence may be multiplexed, thereby effectively reducing a system size and reducing system costs. In addition, the fluorescence and the excitation light pulse train may be further collected by using a confocal optical path design, to resolve a problem that collection of the fluorescence and the excitation light pulse train is not stable due to a shift of a focal point position of the excitation light pulse train caused by an environment change, thereby improving detection precision of the water quality detection system.

In addition to the foregoing disposing manner, in a possible implementation of this application, the reflection element may be disposed as a reflector. The reflector may be provided with a through hole, and the excitation light pulse trains of different wavelengths may be emitted into the to-be-detected water sample through the through hole. It may be understood that a radius of the through hole may be slightly greater than a beam radius of the excitation light pulse train, to reduce an energy loss of the excitation light pulse train. In addition, the fluorescence may be reflected by the reflector and then enter the spectrometer, so that the fluorescence can be collected by the spectrometer as much as possible.

Similarly, the reflection element may be alternatively disposed as a coated window plate. The coated window plate includes a main body and a reflective film disposed on the main body, and the excitation light pulse trains of different wavelengths are reflected by the reflective film and then may be emitted into the to-be-detected water sample. In this implementation, an area of the reflective film may be slightly greater than a projection area of the excitation light pulse train on the coated window plate, to reduce an energy loss of the excitation light pulse train. In addition, the fluorescence may be reflected by the main body of the coated window plate and then enter the spectrometer, so that the fluorescence can be collected by the spectrometer.

When the reflection element is disposed as the reflector or the coated window plate, if the focal point of the excitation light pulse train in the sample cell is still located at the bottom of the cell, a reflected excitation light pulse train returns to the light source along an original path, and therefore the reflected excitation light pulse train cannot be collected. Therefore, in a possible implementation of this application, the focal point of the excitation light pulse trains of different wavelengths focused by the first lens assembly may be located in the to-be-detected water sample. In this way, a focusing process of the focal point can be simplified.

In addition, the water quality detection system may further include a fourth lens assembly and a photoelectric detector. The fourth lens assembly is disposed on one side of the excitation light pulse train that passes through the sample cell, so that after passing through the sample cell, the excitation light pulse trains of different wavelengths can be focused by the fourth lens assembly on the photoelectric detector, and the photoelectric detector collects the excitation light pulse trains that pass through the to-be-detected water sample.

In this application, the data processor may be further configured to: obtain an absorption spectrum based on the excitation light pulse trains collected by the photoelectric detector, and obtain the parameter of the to-be-detected water sample based on the absorption spectrum. In addition, the data processor may further obtain a pollution parameter of the water sample by using a chemical metrology analysis algorithm based on both the three-dimensional fluorescence spectrum and the absorption spectrum, to implement fusion measurement of the three-dimensional fluorescence spectrum and the absorption spectrum, so that the obtained pollution parameter of the water sample is more accurate.

According to a second aspect, this application further provides a water quality detection method using the water quality detection system in the first aspect. The water quality detection method may include the following steps.

The light source emits excitation light pulse trains of different wavelengths to the to-be-detected water sample in a time-division manner, to generate fluorescence separately corresponding to the excitation light pulse trains of different wavelengths; the spectrometer receives the fluorescence corresponding to the excitation light pulse trains of different wavelengths, and outputs a fluorescence spectrum based on the fluorescence; and the data processor identifies the to-be-detected water sample based on the fluorescence spectrum, and obtains a parameter of the to-be-detected water sample.

In a possible implementation of this application, the water quality detection method may further include: The data processor obtains an absorption spectrum based on the excitation light pulse trains of different wavelengths that pass through the to-be-detected water sample, and obtains the parameter of the to-be-detected water sample based on the absorption spectrum.

According to the water quality detection method provided in this application, a change of a water quality model (a pollution component in a water sample) can be monitored while a key pollutant parameter of water quality is measured, and a warning function is provided, to remind operation and maintenance personnel to calibrate a device in a timely manner, thereby avoiding a detection failure of the water quality detection system when the water quality model changes. Therefore, universality of the water quality detection system is improved.

According to a third aspect, this application further provides an electronic device. The electronic device may be but is not limited to a desktop detector or a handheld detector. The electronic device is equipped with the water quality detection system provided in the first aspect, to measure a water quality parameter, and further monitor a change of a water quality model, and a warning function is provided, to remind operation and maintenance personnel to calibrate a device in a timely manner, thereby avoiding a detection failure of the water quality detection system when the water quality model changes. Therefore, universality of the electronic device in the field of water quality detection is improved.

In addition, based on a principle of water quality detection by the electronic device provided in this application, through the proper design, the electronic device may be further used in a field such as medical detection or substance content detection of an agricultural product, to further improve universality of the electronic device.

6

Figure 9:
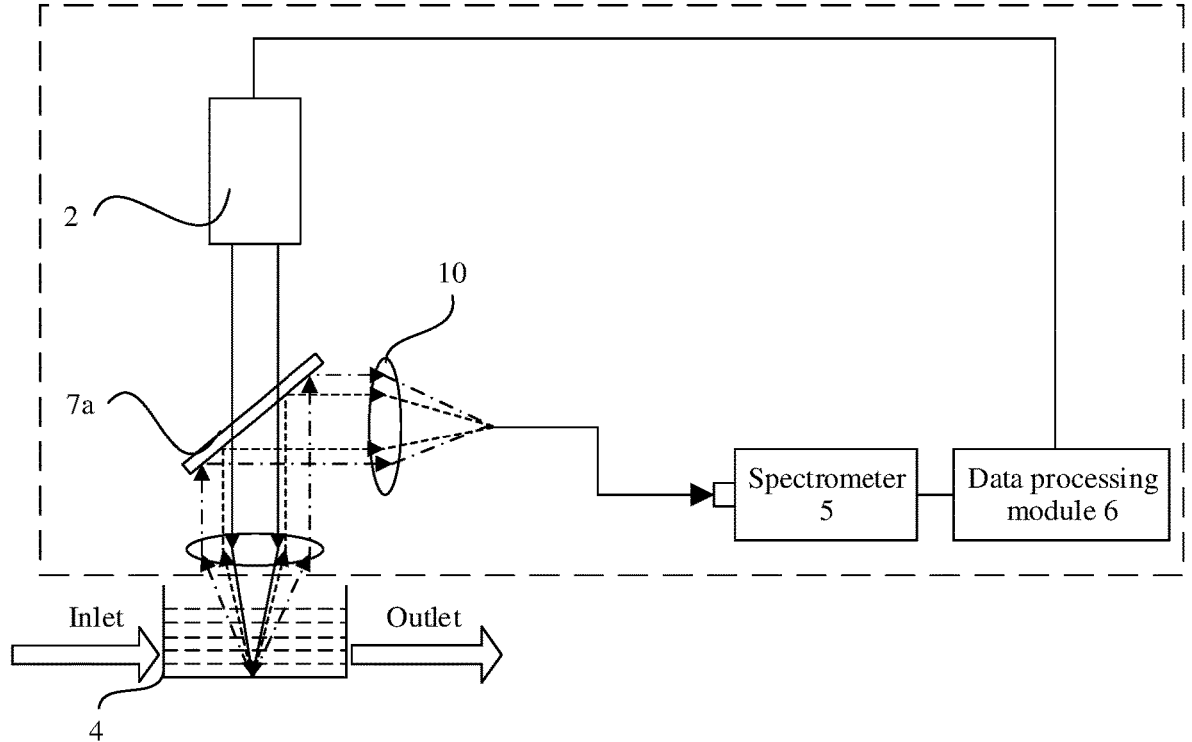
Figure 10:
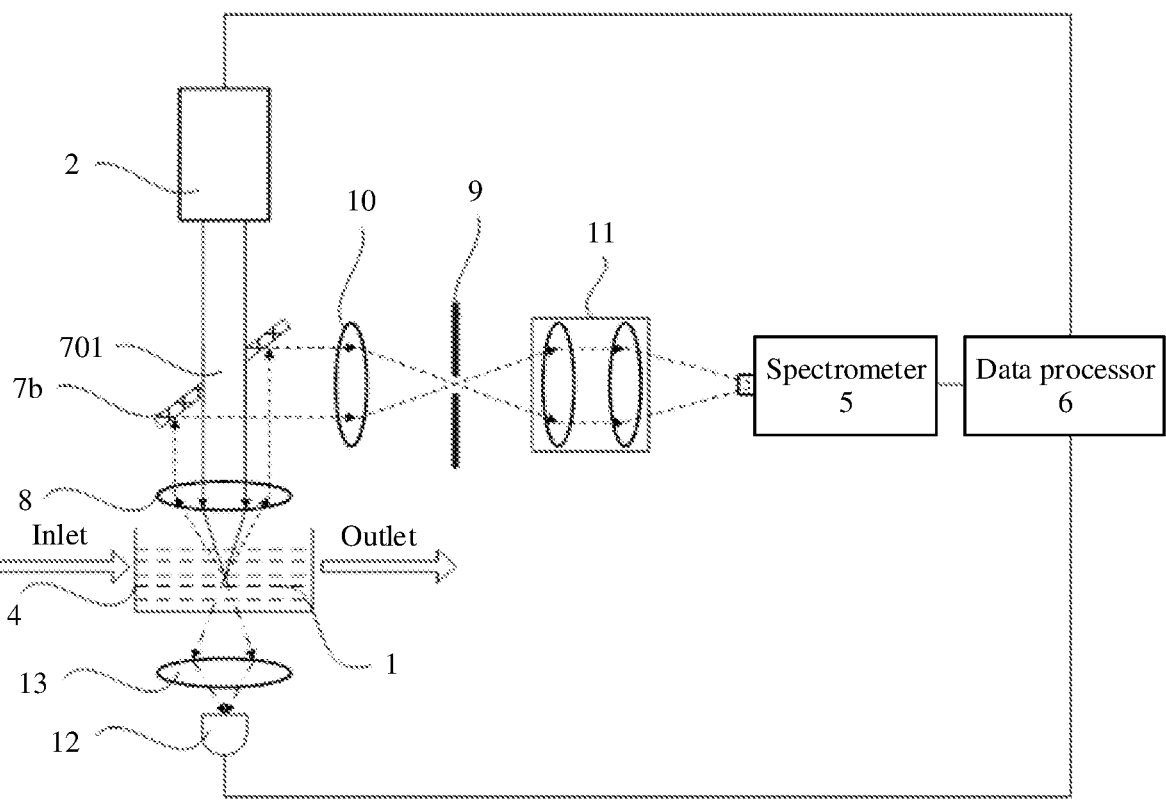
Figure 11:
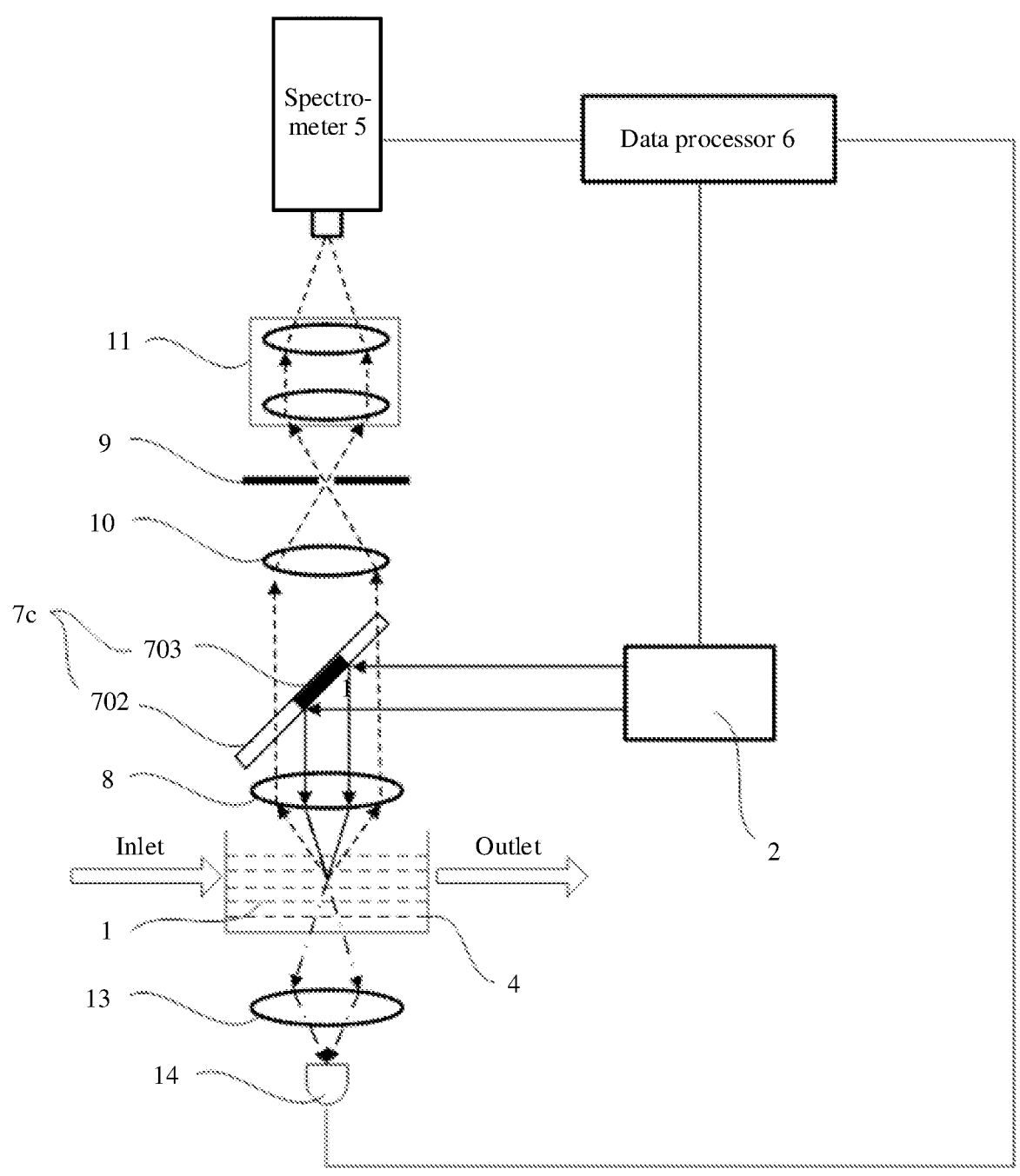

FIG. 9 is a schematic diagram of a structure of a water quality detection system according to another embodiment of this application;

FIG. 10 is a schematic diagram of a structure of a water quality detection system according to another embodiment of this application; and FIG. 11 is a schematic diagram of a structure of a water quality detection system according to another embodiment of this application.

REFERENCE NUMERALS

1: to-be-detected water sample; 2: light source; 201: LED; 202: fiber optic; 203: lens apparatus; 3: optical receiver; 4: sample cell;

5: spectrometer; 6: data processor; 7: reflection element; 7a: beam splitter; 7b: reflector; 701: through hole;

7c: coated window plate; 702: main body; 703: reflective film; 8: first lens assembly; 9: pinhole filter; 9o1: pinhole;

10: second lens assembly; 11: third lens assembly; 12: photoelectric detector; 13: fourth lens assembly.

DETAILED DESCRIPTION OF ILLUSTRATIVE EMBODIMENTS

To facilitate understanding of a water quality detection system provided in embodiments of this application, some application scenarios of the water quality detection system are first described below.

The water quality detection system provided in the embodiments of this application may be applied to any scenario in which water quality detection needs to be performed. For example, the water quality detection system may be applied to a factory sewage outlet and a water source.

Rapid development of industrial production has not only brought about rapid development of social economy, but also caused some degree of pollution to an environment for people's survival, especially water environment pollution. Water environment pollution is becoming increasingly severe and poses a threat to human health and ecological security. For abatement of water environment pollution, first, it is required to establish an online monitoring system for key observation sites (including a key pollution source and a basin observation site) to monitor a pollution situation continuously and automatically. At present, this online monitoring system mainly monitors comprehensive indexes of water quality, such as temperature, chromaticity, turbidity, a pH value, conductivity, a chemical oxygen demand (COD), a biochemical oxygen demand (BOD), total phosphorus (TP), total nitrogen (TN), or ammonia nitrogen. Key pollution indexes such as a COD, a BOD, TP, and TN are measured by using a chemical method. That is, a chemical reagent is placed in a water sample, so that a chemical component in the water sample reacts with the chemical reagent. Then, content of a to-be-detected polluted substance is deduced by measuring a reactant. An advantage of the foregoing chemical method is that the method is highly reliable, but a measurement process of the method is relatively complex, and a measurement time is usually as long as several hours. Therefore, real-time measurement cannot be implemented. In addition, measurement through the chemical method produces a lot of chemical waste liquids, which easily causes secondary pollution and high operation and maintenance costs.

Compared with the chemical method, an emerging spectral analysis method in recent years has remarkable advantages such as fast and real-time measurement, no pollution, and low operation and maintenance costs, and has been widely concerned. In a spectrum detection method, ultraviolet light, visible light, or near-infrared light is mainly used to interact with a pollutant in water, and then a concentration of the pollutant is deduced by measuring light absorption (or generated fluorescence or Raman scattering) of the pollutant. However, components of the pollutant in water are often very complex. For example, measurement of a COD is mainly measurement of a quantity of organic pollutants. There are numerous types of organic pollutants in water, ranging from hundreds or even more. Therefore, content of various organic components in water cannot be measured by using a simple light absorption (or generated fluorescence or Raman scattering) formula. Total content of the pollutant in water can only be predicted by measuring an optical response of the pollutant in a series of water samples (a training set of water samples) to a specified spectral band and by using methods such as a chemical metrology analysis algorithm to establish a mathematical prediction model. This metrology method is essentially to establish a mathematical correspondence between an intensity of light absorption (or generated fluorescence or Raman scattering) and a concentration of a pollutant for specific water quality (water quality with a constant proportion of pollution components in water) and predict a total quantity of pollutants based on the correspondence. Therefore, in comparison with the chemical method, a main disadvantage of the spectrum detection method is that the method is not universal. Especially when water quality pollution components change apparently, the originally established prediction model needs to be recalibrated (recalibration is to measure a spectral response through re-adoption of a training set of water samples and establish a mathematical prediction model by using methods such as a chemical metrology analysis algorithm). Otherwise, a parameter measured by a spectrum detection device may deviate greatly or even become meaningless. However, in a real water environment such as a river basin, a water quality model at a same site may change with time, and this change may occur in an unforeseeable case, thereby causing a failure of an entire spectrum detection device system.

In view of the above, although the spectrum detection method has incomparable advantages (fast and real-time measurement, no pollution, and low costs) over the chemical method, the spectrum detection method has the technical bottleneck of poor universality. Therefore, an existing spectrum detection device is used in only places with relatively stable water quality components, such as a factory sewage outlet and a water source, and cannot be widely used.

Based on this, the embodiments of this application provide a water quality detection system. On the basis of measuring a water quality pollution parameter based on an absorption spectrum (or a fluorescence spectrum) and a chemical metrology analysis algorithm, the water quality detection system integrates a three-dimensional fluorescence spectrum function that can identify a water quality change and issue a warning. While measuring a water quality parameter by using the absorption spectrum (or the fluorescence spectrum), the water quality detection system may determine whether a water quality model (a water quality pollution component or a water quality pollution component proportion) changes by using a three-dimensional fluorescence fingerprint characteristic. If the water quality model changes, the water quality detection system may actively identify this change and issue a warning, where a warning manner may be but is not limited to a sound warning, a light warning, or the like, to remind operation and maintenance personnel to re-collect a training set of water samples to generate a new water quality prediction mathematical model, and re-calibrate the water quality detection system, thereby ensuring normal running of the water quality detection system. In this way, applicable scenarios of the water quality detection system are effectively expanded.

In addition, considering that different water quality models correspond to different three-dimensional fluorescence fingerprint characteristics, after a long period of data accumulation, three-dimensional fluorescence characteristic data of a plurality of water quality models and corresponding mathematical model databases for water quality spectrum prediction may be obtained. In this way, when a water quality model changes, a big data system may be used to automatically replace a mathematical model for water quality spectrum prediction, thereby obtaining a real-time, online, and automatic water quality spectrum detection system that does not require manual calibration.

To make objectives, technical solutions, and advantages of this application clearer, the following further describes this application in detail with reference to the accompanying drawings and specific embodiments.

Terms used in the following embodiments are merely intended to describe specific embodiments, but are not intended to limit this application. Terms "one", "a", "the foregoing", "the", and "the one" of singular forms used in this specification and the appended claims of this application are also intended to include plural forms like "one or more", unless otherwise specified in the context clearly. It should be further understood that in the following embodiments of this application, "at least one" and "one or more" refer to one, two, or more. The term "and/or" is used to describe an association relationship between associated objects and represents that three relationships may exist. For example, A and/or B may represent the following cases: Only A exists, both A and B exist, and only B exists, where A and B each may be singular or plural. The character "/" generally indicates an "or" relationship between the associated objects.

Reference to "an embodiment", "some embodiments", or the like described in this specification indicates that one or more embodiments of this application include a specific characteristic, structure, or characteristic described with reference to the embodiments. Therefore, statements such as "in an embodiment", "in some embodiments", "in some other embodiments", and "in other embodiments" that appear at different places in this specification do not necessarily mean reference to a same embodiment, instead, they mean "one or more but not all of embodiments", unless otherwise specifically emphasized. The terms "include", "contain", "have", and their variants all mean "include but are not limited to", unless otherwise specifically emphasized.

Figure 1:
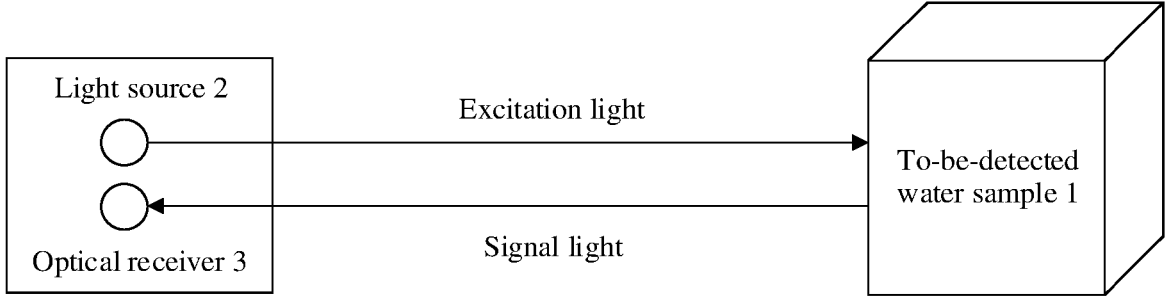
FIG. 1 is a schematic diagram of an application scenario of a water quality detection system according to an embodiment of this application.

As shown in FIG. 1, FIG. 1 is a schematic diagram of an application scenario of a water quality detection system according to a possible embodiment of this application. The water quality detection system may be applied to detection of a parameter of a water quality pollutant, and an application scenario of the water quality detection system may be but is not limited to a basin observation site such as a river or a lake, or a water quality monitoring site such as a factory sewage outlet or an end of an urban household wastewater pipe network. During specific use, an appropriate amount of a to-be-detected water sample 1 may be extracted first; then excitation light emitted by a light source 2 is used to irradiate the to-be-detected water sample 1, and signal light generated through excitation is received by an optical receiver 3; and finally, a spectral characteristic of the signal light is analyzed to obtain a parameter index of a pollutant in the monitored water sample, and a pollution component of the water sample is determined, to implement online water quality spectrum monitoring.

Figure 2:
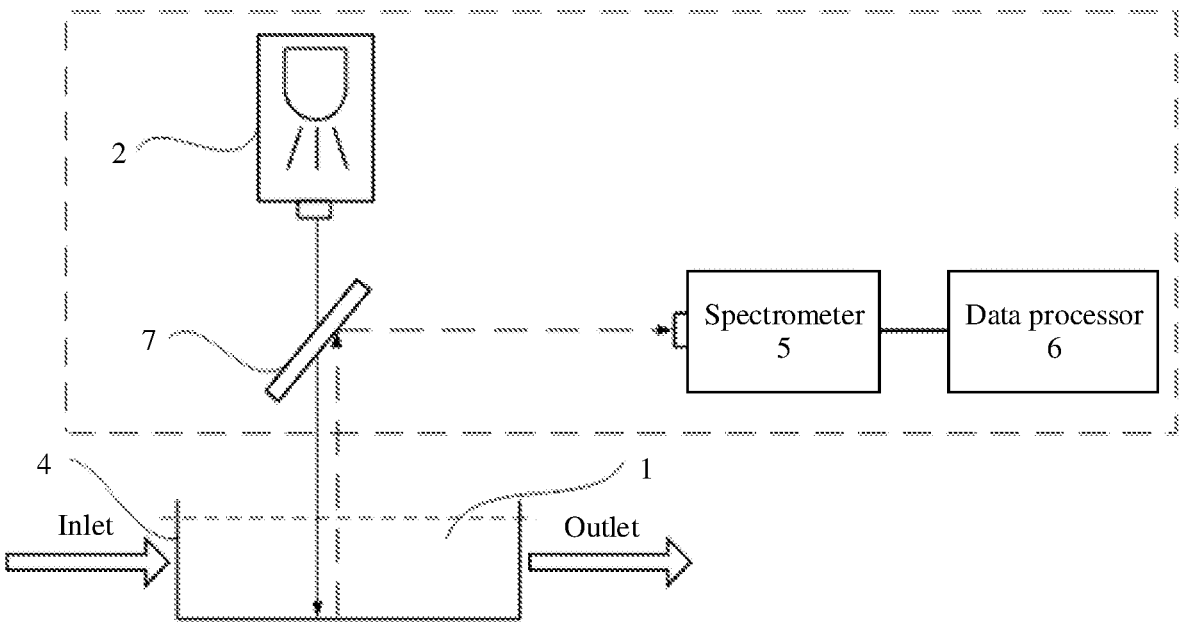
FIG. 2 is a schematic diagram of a structure of a water quality detection system according to an embodiment of this application.

With reference to FIG. 2, FIG. 2 is a schematic diagram of a structure of a water quality detection system according to a possible embodiment of this application. The water quality detection system may include a light source 2, a spectrometer 5, and a data processor 6. It may be understood that parts in a dashed-line box in FIG. 2 represent the water quality detection system. The light source 2 may emit excitation light to a sample cell 4. The sample cell 4 has an inlet and an outlet. The to-be-detected water sample 1 may enter the sample cell 4 through the inlet, and is discharged from the sample cell 4 through the outlet. In addition, the sample cell 4 may be disposed as a structure with an open end. In this way, the light source 2 may be disposed on, but is not limited to, an open side of the sample cell 4, so that the excitation light emitted by the light source 2 is emitted into the sample cell 4.

Figure 3:
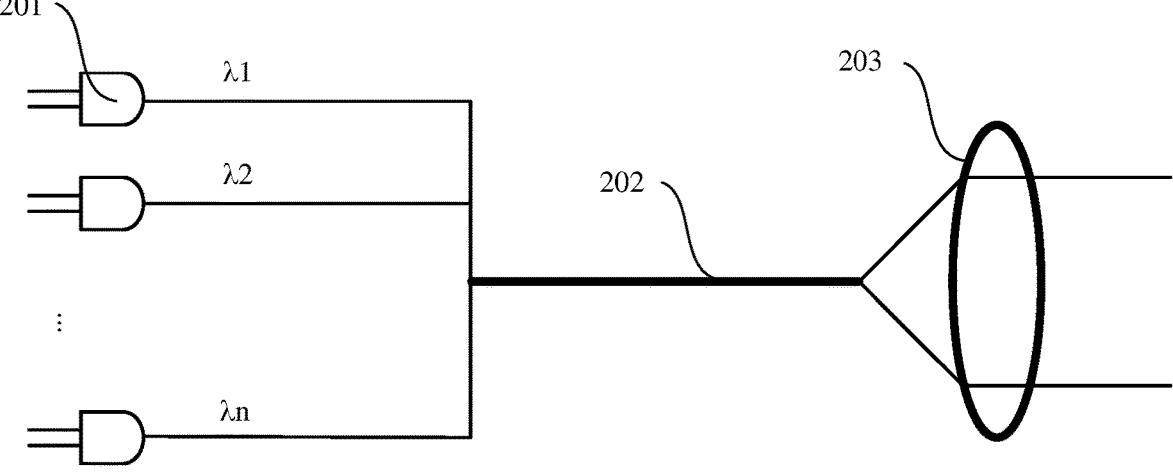
FIG. 3 is a schematic diagram of a structure of a light source according to an embodiment of this application.

In the embodiments of this application, the light source 2 may be a wide-spectrum light source. The wide-spectrum light source may be a continuous-spectrum light source such as a conventional xenon lamp or a deuterium halogen lamp, or may be a light source based on a semiconductor monochromatic laser diode (LD) array or a monochromatic light emitting diode (LED) array. For the continuous-spectrum light source such as a xenon lamp or a deuterium halogen lamp, a narrowband filter array may be used to output monochromatic excitation light in a time-division manner. For a monochromatic LD or LED, monochromatic LD or LED arrays of different wavelengths need to be constructed, and beam combination needs to be performed on output light of the LD or LED arrays for output. As shown in FIG. 3, FIG. 3 shows a beam combination optical design of an LD or LED according to a possible embodiment. During specific implementation, an example in which the light source 2 is designed based on an LED array is used for description. Monochromatic light output by different LEDs 201 is separately coupled to fiber optics, and then a plurality of fiber optics are output through a fiber optic beam combining apparatus as one fiber optic 202. Different monochromatic light that is output may be collimated and output through a lens apparatus 203.

Figure 4:
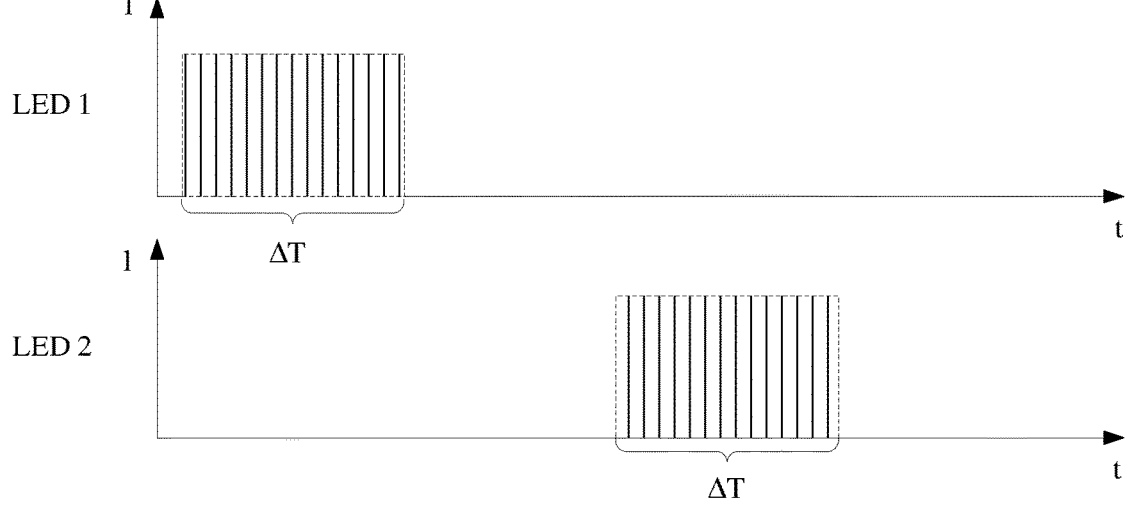
FIG. 4 is a schematic diagram of a driving pulse signal of an LED according to an embodiment of this application.

A power of the LED 201 is usually relatively small, for example, 100 microwatts to 100 milliwatts. Therefore, in order to easily extract a fluorescence signal generated through excitation by excitation light emitted by the LED 201, a drive signal of each LED 201 may further include a series of pulse trains in this application. With reference to FIG. 4, FIG. 4 is a schematic diagram of a driving pulse signal of the LED 201 according to an embodiment. In FIG. 4, a horizontal coordinate represents time, and a vertical coordinate represents a driving pulse intensity. In this embodiment, total duration of a pulse train of a drive signal of each LED 201 may be adjusted based on an intensity of a backward fluorescence signal. In this application, for water quality detection, the total duration $\Delta T$ of the pulse train of the drive signal of each LED 201 is 100 ms to 10 s. For example, the total duration may be set to 500 ms, and a duty cycle of the pulse train may be set to 50%, so that a width of a single pulse is set to 1 ms. Such pulse driving can reduce power consumption of the LED 201 and facilitate heat dissipation of the LED 201. In addition, this pulse modulation mode is conducive to distinguishing and extraction of a weak fluorescence signal from background noise, thereby improving a signal-to-noise ratio of a system.

With reference to FIG. 4 again, in this application, a time interval $\Delta t$ of drive signals that are input into different LEDs 201 may be adjusted based on a specific scenario. The time interval $\Delta t$ is an interval between a cutoff time of inputting a drive signal into a previous LED 201 and a start time of inputting a drive signal into a next LED 201. In a possible embodiment of this application, the time interval $\Delta t$ may be 100 ms to 1 s. For example, the time interval $\Delta t$ may be 500 ms.

In this application, a wavelength of the excitation light emitted by the light source 2 may cover an ultraviolet light band, a visible light band, and an infrared light band. It may be learned from the descriptions of the light source in the foregoing embodiment that, when a drive signal of the light source 2 includes a series of pulse trains, the excitation light emitted by the light source 2 is an excitation light pulse train. Total duration of each excitation light pulse train may be 100 ms to 10 s. For example, the total duration may be set to 500 ms, and a duty cycle of the pulse train may be set to 50%, so that a width of a single pulse is set to 1 ms.

With reference to FIG. 4 again, the to-be-detected water sample 1 is contained in the sample cell 4, and the light source 2 may emit light beams of monochromatic excitation light of different wavelengths to the to-be-detected water sample 1 at an interval of Aa (for example, a wavelength interval of 10 nm). The light source 2 may emit light beams of monochromatic excitation light of at least two different wavelengths to the to-be-detected water sample 1, to excite the to-be-detected water sample 1, and backward fluorescence separately generated by exciting the to-be-detected water sample 1 by the monochromatic excitation light of different wavelengths may be received by the spectrometer 5.

Fluorescence is a luminescence phenomenon of photoluminescence. When being irradiated by incident light (for example, ultraviolet light, visible light, or infrared light) of a specified wavelength, a normal-temperature substance absorbs light energy and enters an excited state, and immediately exits the excited state and emits emergent light of a wavelength greater than that of the incident light (generally, the wavelength is in a visible light band). In this case, the emergent light with this property is called fluorescence. In this application, fluorescence transmitted in a direction opposite to a direction in which the excitation light is incident on the to-be-detected water sample 1 may be referred to as backward fluorescence.

In this application, a time interval $\Delta t$ of emitting monochromatic excitation light of different wavelengths by the light source 2 to the to-be-detected water sample 1 may be adjusted based on a specific scenario. The time interval $\Delta t$ is an interval between a cutoff time of emitting excitation light of a previous wavelength and a start time of emitting an excitation light of a current wavelength in the excitation light of different wavelengths emitted by the light source 2 to the to-be-detected water sample 1. In a possible embodiment, the time interval $\Delta t$ may be 100 ms to 1 s. For example, the time interval $\Delta t$ may be 500 ms. In addition, a wavelength difference between monochromatic excitation light of two wavelengths emitted by the light source 2 at the time interval $\Delta t$ may be 5 nm to 30 nm, for example, 10 nm. On the basis of reducing mutual influence between the excitation light of different wavelengths, backward fluorescence generated by exciting the to-be-detected water sample 1 by excitation light of each wavelength can be obtained.

In order to enable backward fluorescence generated by exciting the to-be-detected water sample 1 by different monochromatic excitation light to be received by the spectrometer 5, a reflection element 7 may be disposed between the light source 2 and the sample cell 4, and the backward fluorescence may be reflected by the reflection element 7 and then enter the spectrometer 5.

It may be understood that, for specific monochromatic excitation light, a fluorescence spectrum generated for the monochromatic excitation light is a two-dimensional curve chart, where a z axis corresponds to a fluorescence intensity, and a y axis corresponds to a fluorescence wavelength. In the case of excitation by different monochromatic excitation light, a three-dimensional fluorescence spectrum may be obtained. For the three-dimensional fluorescence spectrum, a wavelength dimension of excitation light is added on the basis of the foregoing two-dimensional fluorescence spectrum. In a three-dimensional fluorescence matrix spectrum (excitation-emission-matrix spectra, EES) formed by the two-dimensional fluorescence spectrum and the wavelength dimension of the excitation light, it is generally specified that an x axis corresponds to an excitation wavelength, a y axis corresponds to a fluorescence wavelength, and a z axis corresponds to a fluorescence intensity.

Because the three-dimensional fluorescence spectrum includes fluorescence data (an excitation wavelength, a fluorescence wavelength, and a fluorescence intensity) of a water sample, the three-dimensional fluorescence spectrum may be used as a characteristic fingerprint of a specific water sample. In this way, when a water quality pollution component or a water quality pollution component proportion changes, an image characteristic of a corresponding three-dimensional fluorescence spectrum also changes. Therefore, whether the water quality pollution component or the water quality pollution component proportion changes can be determined based on the three-dimensional fluorescence spectrum.

In addition, with reference to FIG. 2 again, in a possible embodiment of this application, while the spectrometer 5 receives backward fluorescence, the monochromatic excitation light of different wavelengths reflected by a bottom of the sample cell 4 may also be collected. Therefore, absorption information of the to-be-detected water sample 1 for the excitation light of different wavelengths may also be simultaneously measured. In this case, the water quality detection system provided in this application may simultaneously obtain a three-dimensional fluorescence spectrum and an absorption spectrum through measurement, to implement fusion spectrum measurement of optical path multiplexing. Finally, the data processor 6 may determine, based on a fingerprint characteristic of the three-dimensional fluorescence spectrum, whether the water quality pollution component or the water quality pollution component proportion (water quality model) changes, and may obtain pollution parameter data of the to-be-detected water sample 1 based on the three-dimensional fluorescence spectrum and/or the absorption spectrum by using a chemical metrology analysis algorithm. It should be noted that a parameter value that is of the to-be-detected water sample 1 and that is obtained through analysis by the data processor 6 based on both the three-dimensional fluorescence spectrum and the absorption spectrum may be relatively accurate.

It should be noted that in this application, the data processor 6 may be but is not limited to a central processing unit (CPU), a field programmable logic array (FPGA), a micro control unit (MCU), or the like. This is not specifically limited in this application.

After a detection principle of the water quality detection system provided in this application is comprehended, the following describes some possible specific disposing manners of the water quality detection system provided in this application.

Figure 5:
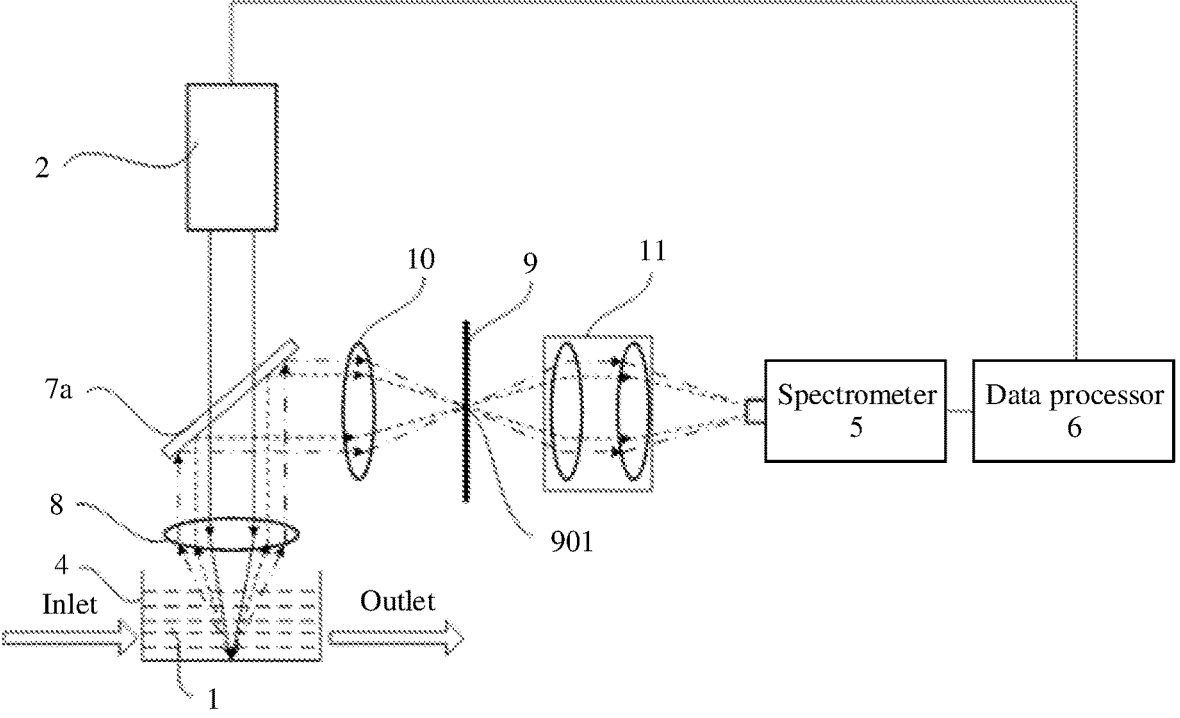
FIG. 5 is a schematic diagram of a structure of a water quality detection system according to another embodiment of this application.

With reference to FIG. 5, FIG. 5 is a schematic diagram of a structure of a water quality detection system according to a possible embodiment of this application. In this embodiment, the reflection element 7 may be a beam splitter 7a (BS), and the beam splitter 7a may change a transmission direction of an optical path. A part of the excitation light of different wavelengths emitted by the light source 2 may be transmitted by the beam splitter 7a, and a part of the excitation light of different wavelengths may be reflected by the beam splitter 7a. In FIG. 5, a solid line with an arrow is used to represent excitation light transmitted by the beam splitter 7a. It may be understood that the excitation light emitted by the light source 2 is an excitation light beam with a specific radius. For ease of expression, in the embodiment shown in FIG. 5, two solid lines with arrows may be used to represent edges of the excitation light beam.

In addition, a first lens assembly 8 may be further disposed between the beam splitter 7a and the sample cell 4, and the first lens assembly 8 may be configured to focus, on the sample cell 4, the excitation light transmitted by the beam splitter 7a. In the embodiment shown in FIG. 5, a focal point of the excitation light focused by the first lens assembly 8 may be located at the bottom of the sample cell 4. In this application, the sample cell 4 may be made of a material such as quartz glass, and the bottom of the sample cell 4 may be coated with or plated with a reflective film 703, to adjust a reflectivity, thereby avoiding saturation of reflected light at the spectrometer 5.

It may be understood that in this application, the first lens assembly 8 may include one or more lenses, provided that the excitation light can be focused. In addition, the first lens assembly 8 may include an achromatic lens, so that focal points of the excitation light of different wavelengths focused by the first lens assembly 8 can be basically the same in the sample cell 4, thereby improving detection precision of the water quality detection system.

With reference to FIG. 5 again, a pinhole filter 9 may be further disposed between the beam splitter 7a and the spectrometer 5. In addition, a second lens assembly 10 may be further disposed between the beam splitter 7a and the pinhole filter 9, and the second lens assembly 10 may be configured to converge, on a pinhole 901 (pinhole) of the pinhole filter 9, optical signals reflected by the beam splitter 7a. The second lens assembly 10 may include one or more lenses, and the second lens assembly 10 may also include an achromatic lens.

In a possible embodiment of this application, a third lens assembly 11 may be further disposed between the pinhole filter 9 and the spectrometer 5, and the third lens assembly 11 may be configured to converge, on the spectrometer 5, optical signals transmitted through the pinhole 901 of the pinhole filter 9.

With reference to FIG. 5 again, in this application, the data processor 6 may be further configured to control the light source 2 to emit excitation light or stop emitting excitation light. For example, when the water quality detection system provided in this embodiment is used for water quality detection, after receiving an instruction that is sent by the data processor 6 and that is used for emitting excitation light, the light source 2 outputs monochromatic excitation light of different wavelengths in a time-division manner, where the monochromatic excitation light of different wavelengths may range from ultraviolet light to infrared light. For example, the light source 2 may output monochromatic excitation light of one wavelength every Aa (to obtain a better three-dimensional fluorescence graph, Δλ should not be too large, for example, may be 10 nm).

In addition, the monochromatic excitation light output by the light source 2 in a time-division manner passes through the beam splitter 7a (a part of excitation light is transmitted by the beam splitter 7a and a part of excitation light is reflected by the beam splitter 7a) and then is focused by the first lens assembly 8 on the bottom of the sample cell 4. In this case, backward fluorescence is generated through execution by the excitation light at the focal point at the bottom of the sample cell 4. In FIG. 5, a dotted line with an arrow is used to represent a transmission direction of the backward fluorescence. It may be understood that the backward fluorescence generated through excitation by the excitation light is a fluorescence beam with a specific radius. For ease of expression, in the embodiment shown in FIG. 5, two dotted lines with arrows may be used to represent edges of the fluorescence beam.

With reference to FIG. 5 again, backward fluorescence is transmitted to the first lens assembly 8 in a direction opposite to an incident direction of excitation light, and the backward fluorescence may be collected and collimated by the first lens assembly 8 and then is emitted into the beam splitter 7a. After being reflected by the beam splitter 7a, the backward fluorescence is focused on the pinhole 901 of the pinhole filter 9 through the second lens assembly 10.

Because the bottom of the sample cell 4 has a specific reflectivity, in addition to generating the backward fluorescence through excitation by the excitation light at the focal point at the bottom of the cell, a part of the excitation light may be transmitted by the bottom of the cell, and another part of the excitation light may be reflected by the bottom of the cell. With reference to FIG. 5 again, in this application, a dashed line with an arrow is used to represent excitation light reflected by the bottom of the sample cell 4. The excitation light reflected by the bottom of the cell is an excitation light beam with a specific radius. In the embodiment shown in FIG. 5, two dashed lines with arrows may be used to represent edges of the excitation light beam. It may be understood that a radius of the excitation light reflected by the bottom of the cell is not much different from a radius of excitation light that is incident on the to-be-detected water sample 1. In the embodiment shown in FIG. 5, for ease of expression, edges of two paths of light are staggered for representation.

The excitation light reflected by the bottom of the sample cell 4 may also be collected and collimated by the first lens assembly 8 and sent to the beam splitter 7a, and is reflected by the beam splitter 7a and then is focused by the second lens assembly 10 on the pinhole 901. It may be learned from FIG. 5 that, in this embodiment of this application, the excitation light reflected by the bottom of the cell and the backward fluorescence may be focused on the same pinhole 901.

It should be noted that, in this application, the pinhole 901 and the focal point of the excitation light at the bottom of the sample cell 4 may be conjugated, and this optical path is referred to as a confocal optical path design. Through the confocal optical path design, the pinhole 901 may filter out fluorescence and a background stray light signal that are generated outside the focal point at the bottom of the sample cell 4, so that the collected backward fluorescence is only backward fluorescence excited at the focal point in the to-be-detected water sample 1. In addition, because the excitation light reflected by the bottom of the cell and the backward fluorescence may be focused on the same pinhole 901, the pinhole 901 may also filter out reflected excitation light and a background stray light signal that are generated outside the focal point at the bottom of the sample cell 4, so that the collected reflected excitation light is only excitation light reflected at the focal point in the to-be-detected water sample 1.

Figure 6:
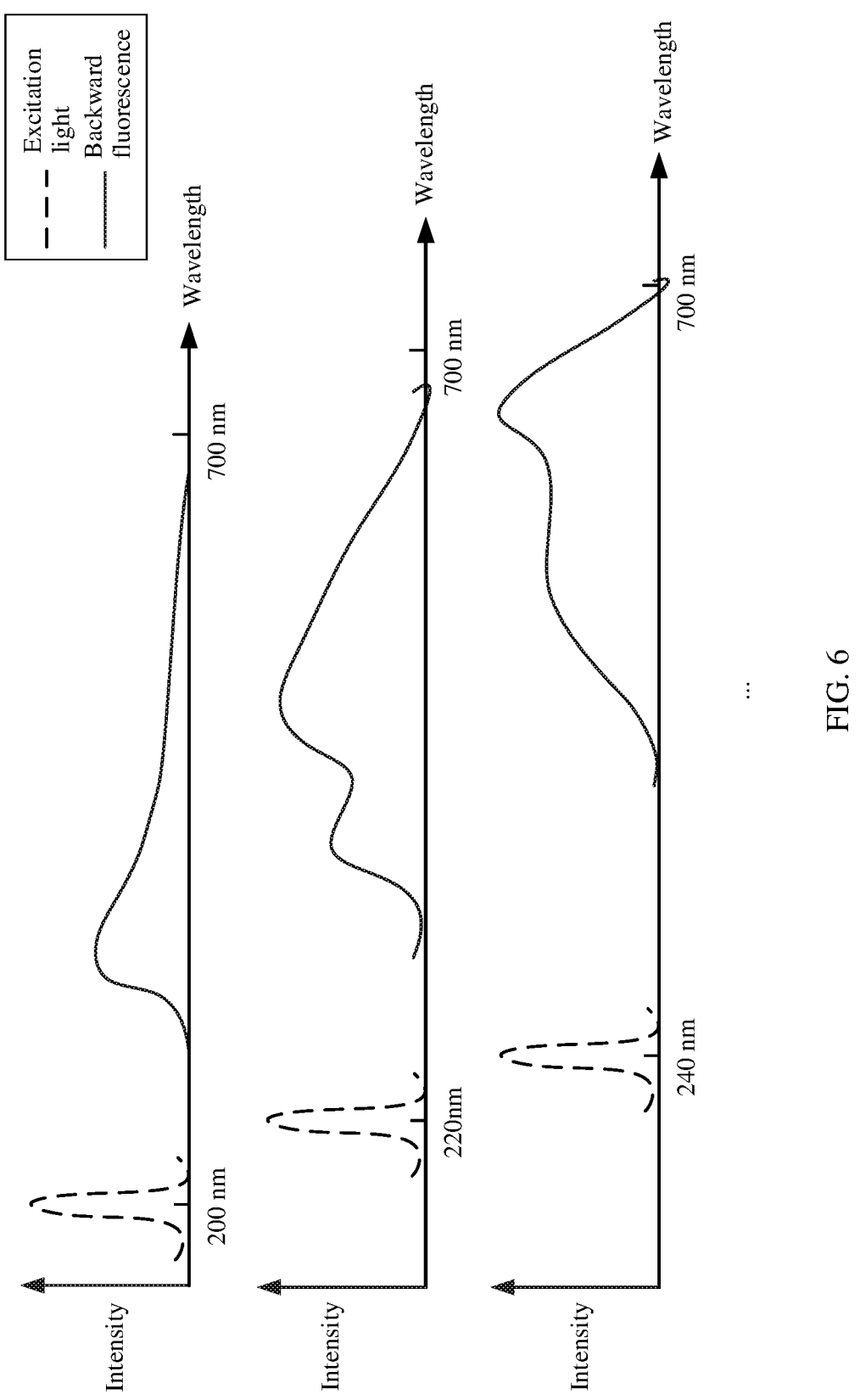
FIG. 6 is a spectrogram of time-division excitation by monochromatic excitation light obtained by a spectrometer according to an embodiment of this application.

After passing through the pinhole 901, the backward fluorescence and the excitation light reflected by the bottom of the cell may be collimated and focused by the third lens assembly 11, and coupled to the spectrometer 5, to obtain spectral data of the backward fluorescence and the reflected excitation light. With reference to FIG. 6, FIG. 6 shows spectral data obtained by the spectrometer 5 according to an embodiment of this application. In FIG. 6, signals of backward fluorescence in the case of excitation by the monochromatic excitation light of different wavelengths and signals of excitation light reflected by the bottom of the sample cell 4 are separately shown from top to bottom. Because a fluorescence wavelength is generally greater than an excitation wavelength, it may be learned from FIG. 6 that a short-band excitation light signal represented by a dashed line and a long-band backward fluorescence signal represented by a solid line are separated in a spectrogram. In other words, through the water quality detection system in this application, fluorescence spectrum information and intensity information of (reflected) excitation light passing through the water sample may be simultaneously obtained through one time of measurement.

Figure 7:
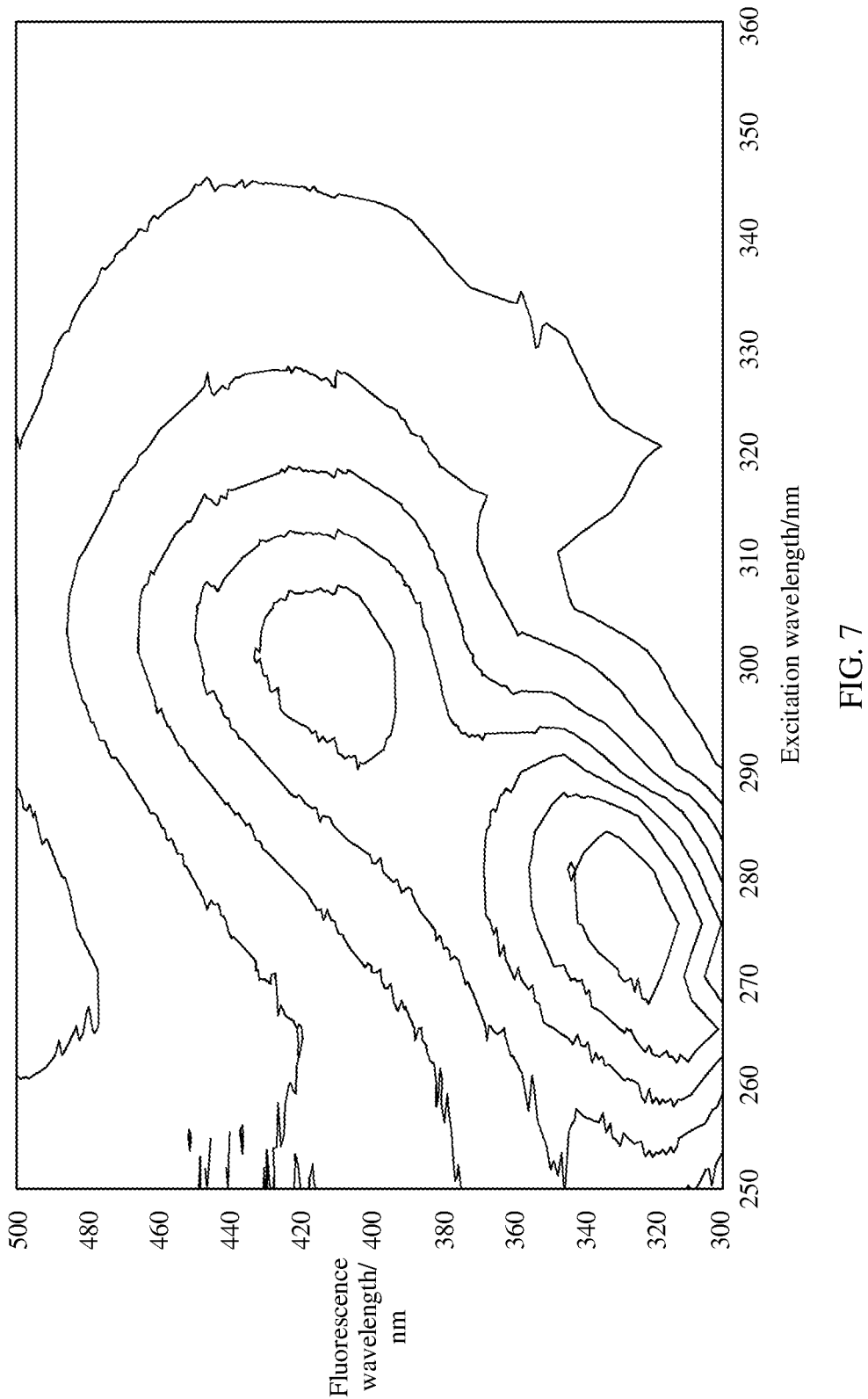
FIG. 7 is a schematic diagram of a three-dimensional fluorescence spectrum according to an embodiment of this application.

For example, with reference to FIG. 6 again, for excitation light of a wavelength of 200 nm, after the reflected excitation light passing through the to-be-detected water sample 1 is received by the spectrometer, a peak value I of a light intensity of the excitation light may be obtained from data of the spectrometer, and a two-dimensional fluorescence spectrum including two dimensions: "fluorescence intensity-fluorescence wavelength" may be obtained. After the to-be-detected water sample 1 is excited by excitation light of all different wavelengths in a time-division manner, a series of two-dimensional fluorescence spectra shown in FIG. 6 may be obtained. In this way, a three-dimensional fluorescence spectrum including three dimensions "fluorescence intensity-excitation wavelength-fluorescence wavelength" is formed by adding one dimension, namely, an excitation wavelength, to the series of two-dimensional fluorescence spectra. As shown in FIG. 7, FIG. 7 shows a three-dimensional fluorescence spectrum according to an embodiment of this application. In FIG. 7, an x axis corresponds to an excitation wavelength, a y axis corresponds to a fluorescence wavelength, and a contour represents an outline formed by equal fluorescence intensities. In this way, the data processor 6 may determine, based on the three-dimensional fluorescence spectrum, whether the water quality pollution component or the water quality pollution component proportion (water quality model) of the to-be-detected water sample changes, and may further obtain a parameter of the to-be-detected water sample based on the three-dimensional fluorescence spectrum by using the chemical metrology analysis algorithm.

In addition, considering that the excitation light reflected by the bottom of the sample cell 4 passes through the water sample twice, the excitation light carries absorption information of the to-be-detected water sample 1. Therefore, a signal intensity I of excitation light received by the spectrometer 5 may be considered as "transmitted light" that passes through the to-be-detected water sample 1 of a length of 2 L, where L is a depth of the to-be-detected water sample 1 in the sample cell 4.

Figure 8:
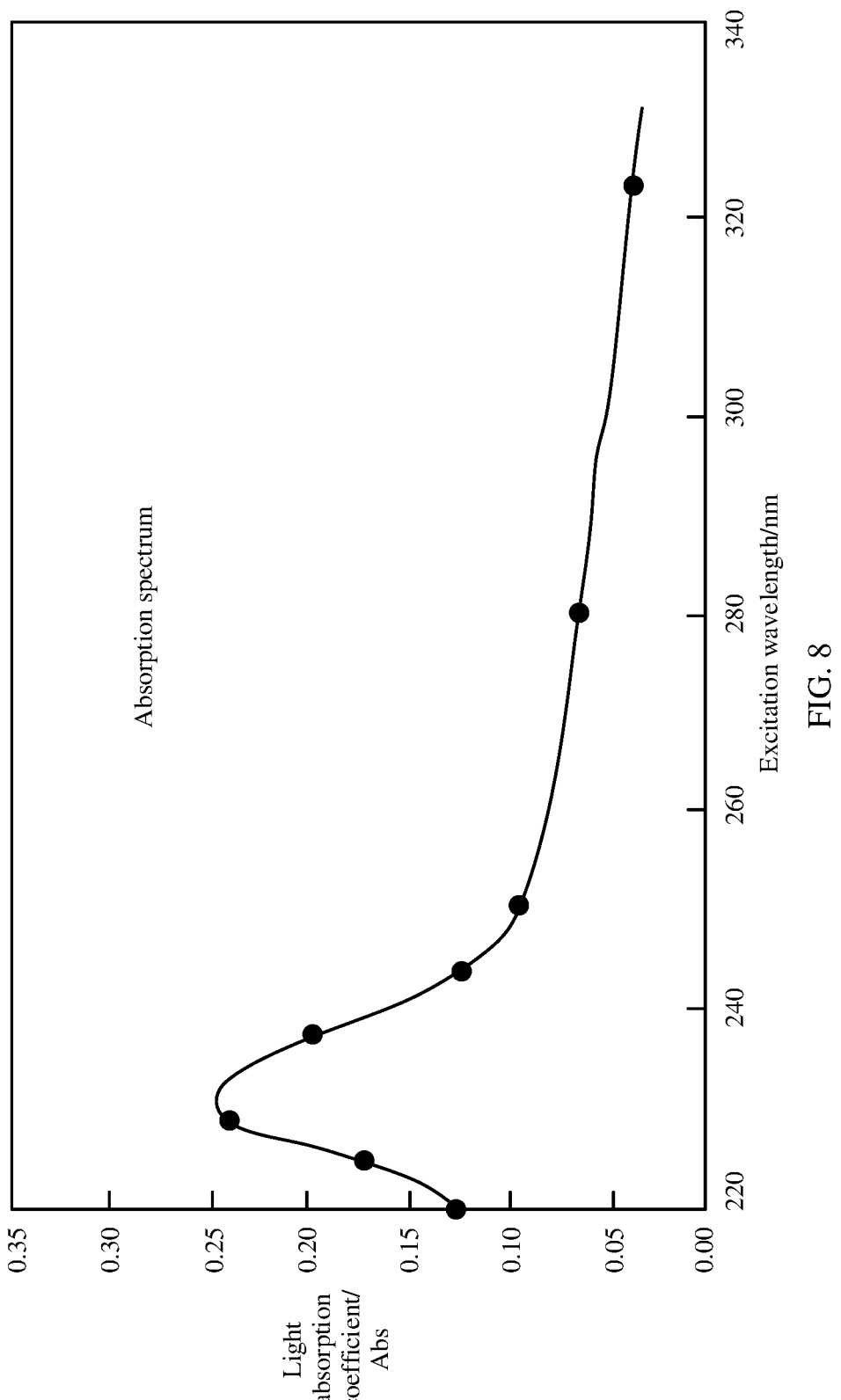
FIG. 8 is a schematic diagram of an absorption spectrum of a water sample according to an embodiment of this application.

In this application, an intensity of the reflected light at the bottom of the empty sample cell 4 may be set to $I_o$ ($I_o$ may be measured and calibrated before the to-be-detected water sample enters). In this case, a light absorption coefficient ε of the to-be-detected water sample may be calculated by using a Beer-Lambert formula $I=I_o \times EXP[-\varepsilon \times 2L]$. In this way, light absorption coefficients of the to-be-detected water sample excited by the excitation light of different wavelengths may be obtained through data processing, so that an absorption spectrum of the to-be-detected water sample shown in FIG. 8 can be obtained. In FIG. 8, horizontal coordinates represent the excitation light of different wavelengths, and vertical coordinates represent light absorption coefficients. Afterwards, the data processor 6 may obtain a pollution parameter of the water sample based on the absorption spectrum by using the chemical metrology analysis algorithm. In addition, the data processor 6 may alternatively obtain the pollution parameter of the water sample based on both the three-dimensional fluorescence spectrum and the absorption spectrum by using the chemical metrology analysis algorithm, to implement fusion measurement of the three-dimensional fluorescence spectrum and the absorption spectrum, so that the obtained pollution parameter of the water sample is more accurate.

According to the water quality detection system provided in this application, fusion measurement of the three-dimensional fluorescence spectrum and the absorption spectrum can be implemented. In addition to measuring a water quality pollution parameter of the to-be-detected water sample, a change of a water quality model of the to-be-detected water sample may be further determined and warned by using the three-dimensional fluorescence spectrum. In addition, the absorption spectrum of the excitation light may be measured through reflection by the bottom of the sample cell 4, and an optical path of the absorption spectrum may be multiplexed with that of the three-dimensional fluorescence spectrum, thereby effectively reducing a system size and reducing system costs.

In addition, in this application, the backward fluorescence and the excitation light are collected by using the confocal optical path design, to resolve a problem that collection of the backward fluorescence and the excitation light is not stable due to a shift of a focal point position of the excitation light caused by an environment change, thereby improving detection precision of the water quality detection system.

In the embodiments of this application, the spectrometer 5 may be a conventional grating-based spectrometer, a fiber optic spectrometer, or various miniaturized spectrometers. For the fiber optic spectrometer 5, a core diameter of a fiber optic at an incident end of the fiber optic spectrometer 5 is generally small (for example, less than 100 microns). With reference to FIG. 9, FIG. 9 is a schematic diagram of a structure of a water quality detection system using a fiber optic spectrometer according to this application. In this embodiment, an incident end of the fiber optic spectrometer may function as the pinhole 901 in the foregoing embodiment. In this way, the pinhole filter 9 and the third lens assembly 11 in the embodiment shown in FIG. 5 may be omitted, thereby simplifying the structure of the water quality detection system. In addition, a specific disposing manner of another part of the water quality detection system shown in FIG. 9 and a water quality detection process are similar to those in the embodiment shown in FIG. 5, and details are not described herein again.

It may be learned from the foregoing descriptions of the water quality detection system provided in this application that the water quality detection system may be divided an optical part and the sample cell 4. With reference to FIG. 9 again, the optical part of the water quality detection system is represented in a dashed-line box in FIG. 9. In this application, the optical part is located on the outside of the sample cell 4, and the optical part and the sample cell 4 may be designed as two parts that can be flexibly disassembled and assembled. In this way, pollution of a device of the optical part by a water sample in the sample cell 4 can be avoided during long-term use. In addition, the sample cell 4 can be cleaned and maintained.

The water quality detection system provided in this application may adopt other possible disposing manners in addition to the disposing manners in the foregoing embodiments. For example, with reference to FIG. 10, FIG. 10 is a schematic diagram of a structure of a water quality detection system according to another possible embodiment of this application. In this embodiment, the reflection element 7 is a reflector 7b, and a through hole 701 is disposed on the reflector 7b. It may be understood that a radius of the through hole 701 may be slightly greater than a radius of a light beam of the excitation light emitted by the light source 2. For example, if the radius of the light beam of the excitation light is 1 mm, the radius of the through hole 701 may be 1.5 mm. In this way, attenuation of energy of the excitation light can be effectively avoided, and the backward fluorescence can be received by the spectrometer 5 as much as possible.

In addition, in some embodiments of this application, a full reflective film may be attached or coated on a surface of one side that is of the reflector 7b and that faces the sample cell 4, to improve reflection efficiency of the backward fluorescence.

The through hole 701 is provided on the reflector 7b, and an optical path is reversible. If a focal point of the excitation light focused by the first lens assembly 8 is still located at the bottom of the sample cell 4, the excitation light returns along an original path and passes through the through hole 701 after being reflected by the bottom of the cell. Therefore, the excitation light cannot be collected. Therefore, in the embodiment shown in FIG. 10, in order to collect the excitation light, the water quality detection system may further be provided with a photoelectric detector 12, where the photoelectric detector 12 may be but is not limited to a photodiode. The sample cell 4 is disposed between the reflector 7b and the photoelectric detector 12, and the photoelectric detector 12 may be further disposed at a pixel position of the focal point of the excitation light in the sample cell.

In addition, in this embodiment of this application, because the excitation light does not need to be reflected by the bottom of the sample cell 4, the first lens assembly 8 may focus the excitation light on the water sample in the sample cell 4, so that the focal point of the excitation light falls in the water sample. In this way, a focusing process of the focal point of the excitation light can be effectively simplified.

With reference to FIG. 10 again, a fourth lens assembly 13 may be further disposed between the sample cell 4 and the photoelectric detector 12, and the fourth lens assembly 13 may be configured to converge, on the photoelectric detector 12, excitation light transmitted by the sample cell 4. The fourth lens assembly 13 may include one or more lenses, provided that the transmitted excitation light can be focused. In addition, the fourth lens assembly 13 may include an achromatic lens, so that focal points of the excitation light of different wavelengths focused by the fourth lens assembly 13 may be basically the same, thereby improving detection precision of the water quality detection system.

In the embodiment shown in FIG. 10, absorption information of the to-be-detected water sample 1 for the excitation light may be collected by using the photoelectric detector 12. During specific implementation, before the water sample is extracted into the sample cell 4, the light source 2 emits the excitation light of different wavelengths according to an instruction sent by the data processor 6, and the photoelectric detector 12 measures a light intensity $I_o$ of excitation light of each wavelength when there is no to-be-detected water sample. After the to-be-detected water sample 1 enters the sample cell 4, the light source 2 emits the excitation light of different wavelengths. In this case, the photoelectric detector 12 measures an optical signal strength I of the excitation light of each wavelength passing through the water sample. Then, a light absorption coefficient c of the to-be-detected water sample 1 may be calculated by using a Beer-Lambert formula $I=I_o \times EXP[-\varepsilon \times L]$, where L is a depth of the water sample. In this way, the data processor may obtain the absorption spectrum shown in FIG. 8 based on the measured light absorption coefficient c of the excitation light of each wavelength.

It may be understood that, in the embodiment shown in FIG. 10, for a specific disposing manner of another structure, refer to the embodiment shown in FIG. 5 or FIG. 9. Details are not described herein again. In addition, in the embodiment shown in FIG. 10, the spectrometer 5 is configured to collect only information about a three-dimensional fluorescence spectrum. A specific collection manner of the spectrometer 5 is similar to that in the foregoing embodiment, and details are not described herein again. The data processor 6 may determine, based on the three-dimensional fluorescence spectrum obtained by the spectrometer 5, whether the water quality pollution component or the water quality pollution component proportion (water quality model) changes, and may further obtain the parameter of the to-be-detected water sample based on the three-dimensional fluorescence spectrum by using the chemical metrology analysis algorithm. It should be noted that the data processor may further obtain the pollution parameter data of the water sample based on the absorption spectrum obtained by the photoelectric detector 12 and by using the chemical metrology analysis algorithm. In addition, the data processor may alternatively obtain the pollution parameter of the water sample based on both the three-dimensional fluorescence spectrum and the absorption spectrum by using the chemical metrology analysis algorithm, to implement fusion measurement of the three-dimensional fluorescence spectrum and the absorption spectrum, so that the obtained pollution parameter of the water sample is more accurate.

With reference to FIG. 11, FIG. 11 is a schematic diagram of a structure of a water quality detection system according to another possible embodiment. A difference between this embodiment and the embodiment shown in FIG. 10 lies in a specific disposing form of the reflection element 7. Specifically, in FIG. 11, the reflection element 7 is a coated window plate 7c, and a main body 702 of the coated window plate 7c is a transparent optical window plate with a wide spectrum (a band from ultraviolet light to near-infrared light), and the main body 702 may be made of, but is not limited to, a fused quartz glass plate. In addition, a reflective film 703 is disposed on the main body 702, and the reflective film 703 may be configured to reflect the excitation light of different wavelengths emitted by the light source 2.

It should be noted that in this embodiment, the reflective film 703 is disposed on one side that is of the main body 702 and that faces the sample cell 4, so that the excitation light emitted by the light source 2 is reflected by the reflective film 703 and then enters the sample cell 4. It may be understood that an area of the reflective film 703 may be adjusted based on a beam radius of the excitation light. For example, the area of the reflective film 703 is slightly greater than an area of a light beam that is of the excitation light and that is incident on the coated window plate 7c, so that a loss of the excitation light at the coated window plate 7c is smaller or even negligible, and the backward fluorescence can be received by the spectrometer 5 as much as possible. In addition, an area of the main body 702 of the coated window plate 7c is far greater than that of the reflective film 703, to reduce attenuation of a backward fluorescence signal due to the reflective film 703 as much as possible.

With reference to FIG. 11 again, in this embodiment of this application, when backward fluorescence generated through excitation by the excitation light of different wavelengths in the to-be-detected water sample 1 is emitted into the coated window plate 7c, except that backward fluorescence emitted into the reflective film 703 is filtered out, remaining backward fluorescence may pass through another part of the main body 702 of the coated window plate 7c and then is collected by the spectrometer 5, to obtain a three-dimensional fluorescence spectrum.

In the embodiment shown in FIG. 11, for a specific disposing manner of another structure, refer to any one of the foregoing embodiments. Details are not described herein again.

According to the water quality detection system provided in this application, a change of a water quality model (a pollution component in a water sample) can be monitored while a key pollutant parameter of water quality is measured, and a warning function is provided, to remind operation and maintenance personnel to calibrate a device in a timely manner, thereby avoiding a detection failure of the water quality detection system when the water quality model changes. Therefore, universality of the water quality detection system is improved.

In this application, a confocal backward fluorescence collection solution avoids a change and movement of a focal point of the excitation light in the to-be-detected water sample due to an external environment change, so that a backward fluorescence signal is collected stably and reliably. In addition, operation and maintenance of the water quality detection system is improved by enabling an optical measurement part and the sample cell 4 to be flexibly disassembled and assembled.

The foregoing descriptions are merely specific implementations of this application, but are not intended to limit the protection scope of this application. Any variation or replacement readily figured out by a person skilled in the art within the technical scope disclosed in this application shall fall within the protection scope of this application. Therefore, the protection scope of this application shall be subject to the protection scope of the claims.

What is claimed is:

1. A water quality detection system, comprising:
a light source, configured to emit a plurality of excitation light pulse trains to a to-be-detected water sample in a time division manner, to generate fluorescence, wherein each excitation light pulse train in the plurality of excitation light pulse trains corresponds to a different wavelength, and each excitation light pulse train corresponds to a respective generated fluorescence;

a reflector disposed along a shortest virtual line between the light source and the to-be-detected water sample, wherein the plurality of excitation light pulse trains are emitted into the to-be-detected water sample through the reflector;

a spectrometer, configured to:

for each excitation light pulse trains in the plurality of excitation light pulse trains, receive the fluorescence corresponding to the respective excitation light pulse train after the fluorescence passes through the reflector; and output a fluorescence spectrum based on fluorescence generated by the plurality of excitation light pulse trains; and a data processor, configured to identify the to-be-detected water sample based on the fluorescence spectrum, and obtain a parameter of the to-be-detected water sample;

wherein for each two sequential excitation light pulse trains in the plurality of excitation light pulse trains, a time interval $\Delta t$ between a cutoff time of emitting an earlier excitation light pulse train corresponding to a first wavelength and a start time of emitting a later excitation light pulse train corresponding to a second wavelength is 100 ms to 1 s; and wherein a wavelength difference between each two sequential excitation light pulse trains emitted by the light source to the to-be-detected water sample $\Delta t$ is 5 nm to 30 nm.

2. The water quality detection system according to claim 1, wherein for each excitation light pulse train in the plurality of excitation light pulse trains, a total duration of emitting the respective excitation light pulse train is 100 ms to 10 s.

3. The water quality detection system according to claim 1, further comprising:

a first lens assembly, configured to focus the plurality of excitation light pulse trains on the to-be-detected water sample.

4. The water quality detection system according to claim 3, further comprising:

a second lens assembly disposed between the reflector and the spectrometer, wherein the second lens assembly is configured to focus the fluorescence reflected by the reflector and input the focused fluorescence into the spectrometer.

5. The water quality detection system according to claim 4, further comprising a pinhole filter, wherein the pinhole filter is disposed between the second lens assembly and the spectrometer, a pinhole extends in the pinhole filter, and the pinhole and a focal point of the plurality of excitation light pulse trains in the to-be-detected water sample are conjugated.

6. The water quality detection system according to claim 5, further comprising:

a third lens assembly disposed between the pinhole filter and the spectrometer, wherein the third lens assembly is configured to collimate and focus fluorescence that passes through the pinhole filter and input the collimated and focused fluorescence into the spectrometer.

7. The water quality detection system according to claim 5, wherein the reflector comprises a beam splitter, the beam splitter is configured to transmit a part of the excitation light pulse trains of the plurality of excitation light pulse trains emitted by the light source, and the beam splitter is configured to reflect the corresponding fluorescence into the spectrometer.

8. The water quality detection system according to claim 7, wherein a focal point of the plurality of excitation light pulse trains focused by the first lens assembly is located at a bottom of a sample cell, wherein the sample cell carries the to-be-detected water sample.

9. The water quality detection system according to claim 8, wherein the spectrometer is further configured to receive the plurality of excitation light pulse trains that are reflected by the bottom of the sample cell and that pass through the to-be-detected water sample; and wherein the data processor is further configured to obtain an absorption spectrum based on the plurality of excitation light pulse trains received by the spectrometer.

10. The water quality detection system according to claim 4, wherein the spectrometer comprises a fiber optic spectrometer, and after being focused by the second lens assembly, the fluorescence reflected by the reflector enters the fiber optic spectrometer through a fiber optic of the fiber optic spectrometer.

11. The water quality detection system according to claim 1, wherein a through hole extends in the reflector, the plurality of excitation light pulse trains are emitted into the to-be-detected water sample through the through hole, and the corresponding fluorescence is reflected by the reflector and then enters the spectrometer.

12. The water quality detection system according to claim 11, wherein a focal point of the plurality of excitation light pulse trains focused by a first lens assembly is located in the to-be-detected water sample.

13. The water quality detection system according to claim 12, further comprising:

a fourth lens assembly; and a photodiode detector; and wherein the fourth lens assembly is disposed on a side of the plurality of excitation light pulse trains that pass through a sample cell that carries the to-be-detected water sample and is configured to focus, on the photodiode detector, the plurality of excitation light pulse trains that pass through the to-be-detected water sample.

14. The water quality detection system according to claim 13, wherein the data processor is further configured to obtain an absorption spectrum based on the plurality of excitation light pulse trains received by the photodiode detector.

15. The water quality detection system according to claim 1, wherein the reflector is a coated window plate, the coated window plate comprises a main body and a reflective film disposed on the main body, and the plurality of excitation light pulse trains of different wavelengths are reflected by the reflective film and are emitted into the to-be-detected water sample, and the corresponding fluorescence is transmitted through the main body and enters the spectrometer.

16. A method, comprising:

emitting, by a light source, a plurality of excitation light pulse trains through a reflector to a to-be-detected water sample in a time division manner, to generate fluorescence, wherein each excitation light pulse train in the plurality of excitation light pulse trains corresponds to a different wavelength, each excitation light pulse train corresponds to a respective generated fluorescence, and the reflector is disposed along a shortest virtual line between the light source and the to-be-detected water sample;

for each excitation light pulse train in the plurality of excitation light pulse trains, receiving, by a spectrometer, the fluorescence corresponding to the respective excitation light pulse train;

outputting, by the spectrometer, a fluorescence spectrum based on the fluorescence generated by the plurality of excitation light pulse trains; and identifying, by a data processor, the to-be-detected water sample based on the fluorescence spectrum, and obtaining a parameter of the to-be-detected water sample;

wherein for each two sequential excitation light pulse trains in the plurality of excitation light pulse trains, a time interval $\Delta t$ between a cutoff time of emitting an earlier excitation light pulse train corresponding to a first wavelength and a start time of emitting a later excitation light pulse train corresponding to a second wavelength is 100 ms to 1 s; and wherein a wavelength difference between each two sequential excitation light pulse trains emitted by the light source to the to-be-detected water sample $\Delta t$ is 5 nm to 30 nm.

17. The method according to claim 16, further comprising:

obtaining, by the data processor, an absorption spectrum based on the plurality of excitation light pulse trains that pass through the to-be-detected water sample, and obtaining the parameter of the to-be-detected water sample based on the absorption spectrum.

18. The method according to claim 16, further comprising:

focusing, by a first lens assembly, the plurality of excitation light pulse trains on the to-be-detected water sample.

19. The method according to claim 16, wherein for each excitation light pulse train in the plurality of excitation light pulse trains, a total duration of emitting the respective excitation light pulse train is 100 ms to 10 s.

20. The method according to claim 16, wherein the plurality of excitation light pulse trains are focused on the to-be-detected water sample by a first lens assembly.

* * * * *